United States Patent
Culjak

[19]

[11] Patent Number: 6,003,744
[45] Date of Patent: Dec. 21, 1999

[54] LUMBAR OXYGEN CARRIER

[76] Inventor: Iolanthe Culjak, P.O. Box 3353, Estes Park, Colo. 80517

[21] Appl. No.: 09/053,215

[22] Filed: Apr. 1, 1998

[51] Int. Cl.[6] ...................................................... A45F 5/00
[52] U.S. Cl. .................................... 224/148.5; 224/148.2; 224/583; 224/625; 224/674; 224/676; 128/205.22
[58] Field of Search ............................ 224/148.1, 148.2, 224/148.4–148.7, 191, 605, 625, 626, 660, 662, 663, 665, 674, 675, 676, 235, 240, 250, 575, 581, 582, 583, 652, 153, 255; 128/205.22

[56] References Cited

U.S. PATENT DOCUMENTS

| | | | |
|---|---|---|---|
| 756,177 | 3/1904 | Mills | 224/660 X |
| 2,625,192 | 1/1953 | Kinskie | 224/665 |
| 4,739,913 | 4/1988 | Moore | 224/652 X |
| 4,878,606 | 11/1989 | Miller | 224/625 |
| 5,228,609 | 7/1993 | Gregory | 224/625 X |
| 5,240,156 | 8/1993 | Sicotte et al. | 224/148.5 X |
| 5,267,679 | 12/1993 | Kamaya et al. | 224/583 |
| 5,400,934 | 3/1995 | Ducros | 224/148.2 |

FOREIGN PATENT DOCUMENTS

| | | | |
|---|---|---|---|
| 57338 | 2/1940 | Denmark | 224/209 |
| 154365 | 7/1932 | Switzerland | 224/153 |

*Primary Examiner*—Gregory M. Vidovich
*Attorney, Agent, or Firm*—John P. Halvonik

[57] ABSTRACT

The invention is a lumbar supported carrier for oxygen tanks comprising a main belt portion and a pouch for the tank. The belt has a shoulder strap for stabilizing the belt and tank extending over the shoulder and diagonally across the body. The shoulder strap comes with a series of smaller straps for securing the hose or cannula that is used in connection with the tank. The pouch is attachable to the belt by means of straps and has a drawstring with cord lock for securing the tank within the pouch. In addition, the pouch has separate D rings that allow the pouch to be attached to the shoulder strap and used separately from the belt. The belt has a padded portion to fit the curve of the lumbar area of the human spine.

3 Claims, 6 Drawing Sheets

LUMBAR OXYGEN CARRIER

FIELD OF THE INVENTION

The invention relates to the field of supports and in particular to a support for an oxygen bottle and accompanying cannula that is designed to be supported by the lumbar region of the back and having a shoulder strap for support of the device.

BACKGROUND OF THE INVENTION

There are many people nowadays who need to transport a secondary supply of oxygen for their needs. Such supplies take the form of an oxygen tank with related features for distributing the oxygen e.g. a face mask and a cannula to bring the oxygen from the tank to the nostrils of the patient. Such tanks can be quite heavy to carry around and may result in the patient doing permanent damage to his or her back or shoulder.

The invention herein described is believed to help those patients better able to transport their supply of oxygen by distributing the weight of the oxygen tank more evenly upon the body and in particular to allow the pelvic region of the body to support the majority of the weight of the bottle. The back of the belt is padded to further facilitate the resting of the tank against the user's back. A pouch feature is used in connection with the belt and has its own means for attaching to the belt. The pouch includes a draw string to further secure the tank in the pouch.

Additional features of the invention allow for adjustment of the strap that accompanies the support as well as allowing the user to detach the pouch portion of the apparatus from the belt and be used separately by attaching the pouch to the shoulder strap that is detached from the belt. Other features allow the hose to be attached to several places on the shoulder strap and prevent it from being caught on small objects. After removing the belt with the tank, the tank may easily be rested in an upright position to allow use of the oxygen while having the tank sitting beside the user. The belt itself is also adjustable to accommodate the different waist sizes of the users.

DESCRIPTION OF THE PRIOR ART

There are no known devices that allow for lumbar support of an oxygen tank with a separate pouch for securing the tank. Other features including detachable straps and clips for the belt are also believed to be novel in connection with oxygen tank supports.

SUMMARY OF THE INVENTION

The invention is a lumbar supported carrier for oxygen tanks comprising a main belt portion and a pouch in connection with the belt and at the rear of the belt. The pouch is detachable from the belt by means of straps that are directly attached to the belt and can be secured to the pouch when needed. The belt has a shoulder strap for stabilizing the belt and tank over the shoulder and diagonally across the body. There is no pressure felt by the user as all the weight is carried at the pelvis of the user.

The shoulder strap comes with a series of smaller straps for securing the hose that is used in connection with the tank. The shoulder strap is detachable for use separate from the belt. The pouch is attachable to the belt by means of straps and has a drawstring with cord lock for securing the tank within the pouch. In addition, the pouch has separate D rings that allow the pouch to be attached to the shoulder strap and used separately from the belt.

It is an objective to provide a lumbar based support for oxygen tanks that can support the weight of an oxygen tank in a manner that allows the tank to be easily transportable and with minimal strain on the back or shoulders.

It is another objective to provide a lumbar based support for oxygen tanks that can be quickly disconnected from the user's torso when it is desired to take the tank off.

Another objective is to provide a lumbar based support for oxygen tanks with a separate pouch for the tank that can be detached from the belt when needed and used with a separate shoulder strap apart from the belt.

Another objective is to provide a lumbar based support for oxygen tanks that allows the hose from the tank to be attached to a shoulder strap to prevent the hose from catching on objects or otherwise being a nuisance.

Other objects will be apparent once the invention is shown and described.

DESCRIPTION OF THE PREFERRED EMBODIMENT

Figure 1:
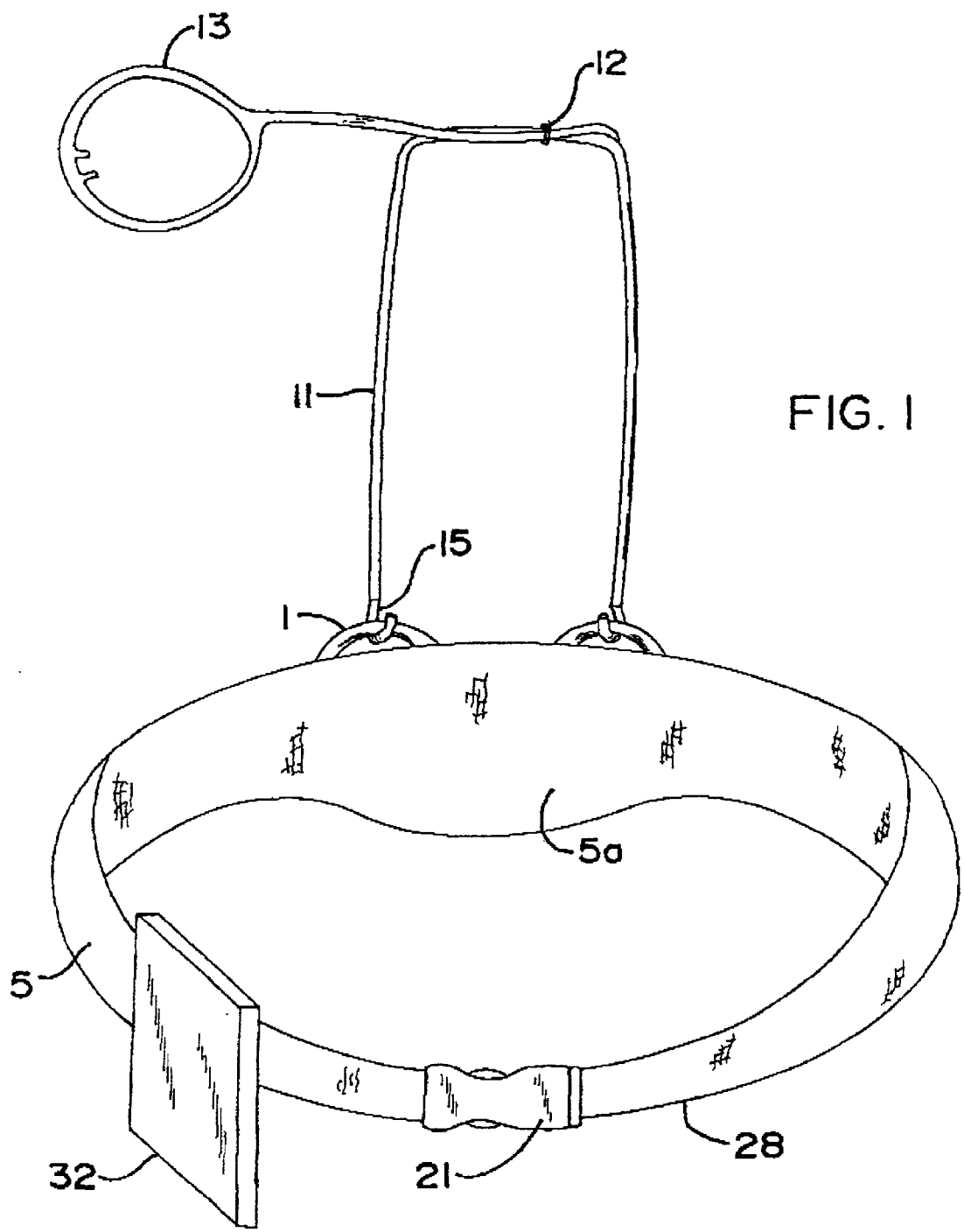
FIG. 1 is a front view of belt and shoulder strap.

The overall construction of the lumbar oxygen carrier is as shown in FIG. 1. The main portion of the carrier will take the form of a padded belt 5 having a pouch 6. The belt should be of shape and size so that it may go around the waist of the patient and to be secured to the front of the waist in the manner of a belt. The belt is a single piece of material with heavy fabric, leather, or similar materials that can be used for this purpose. The front of the belt 28 should have a quick release buckle 21 (see FIGS. 1 and 4) so that the user can quickly detach the belt from his/her waist as necessary.

Figure 2:
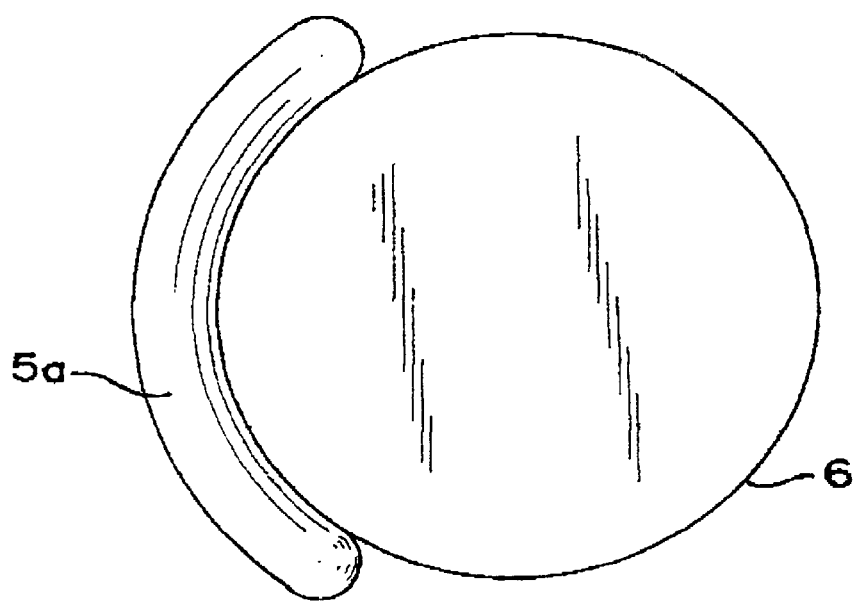
FIG. 2 is a side view of belt and pouch with tank.
Figure 3:
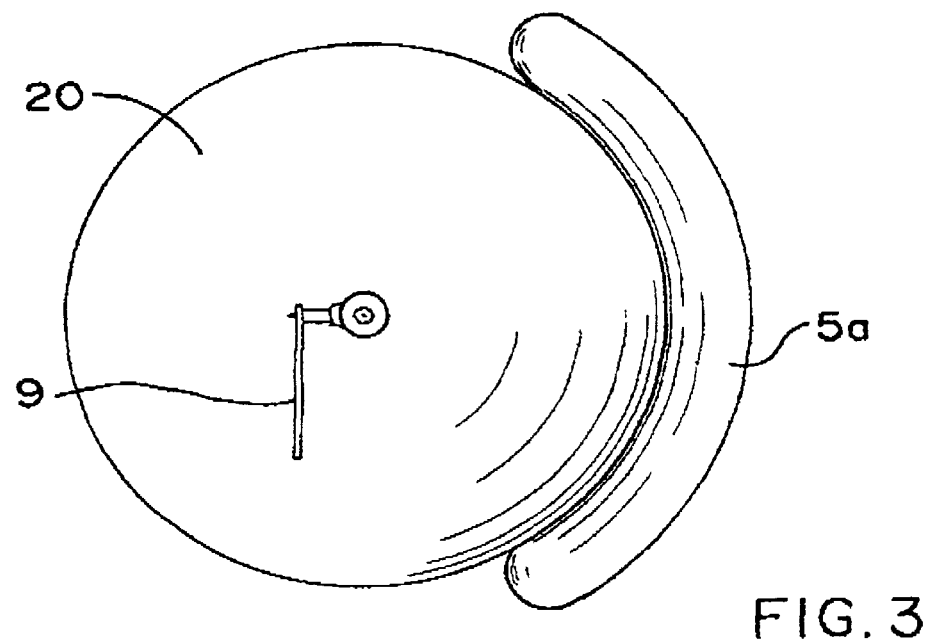
FIG. 3 is a side view of pouch and tank (it is noted that elements: 1, 1a, 2, 3, and 4 are omitted from FIGS. 2 and 3 for purposes of clarity)
Figure 4:
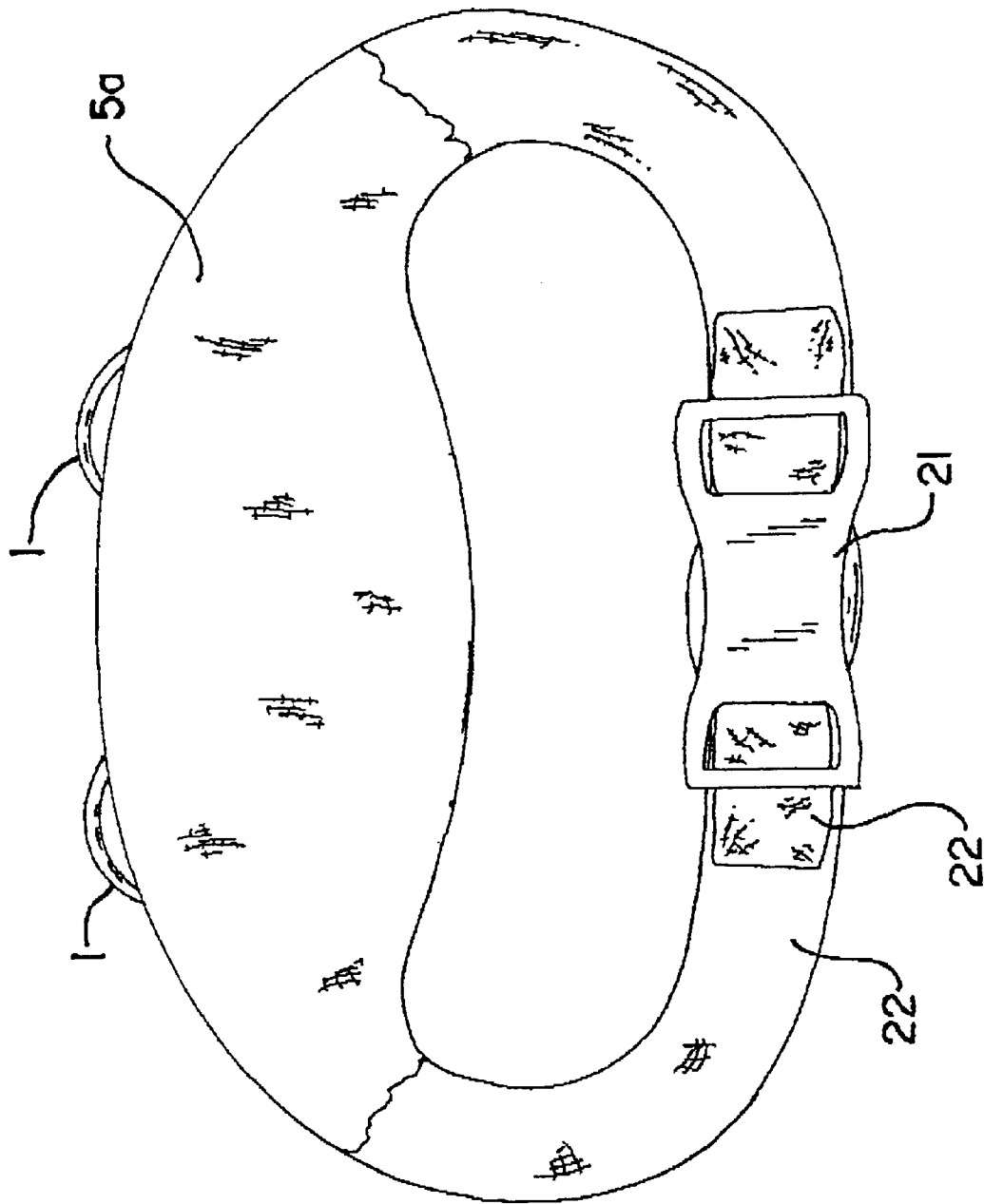
FIG. 4 is a front view of lumbar carrier.
Figure 5:
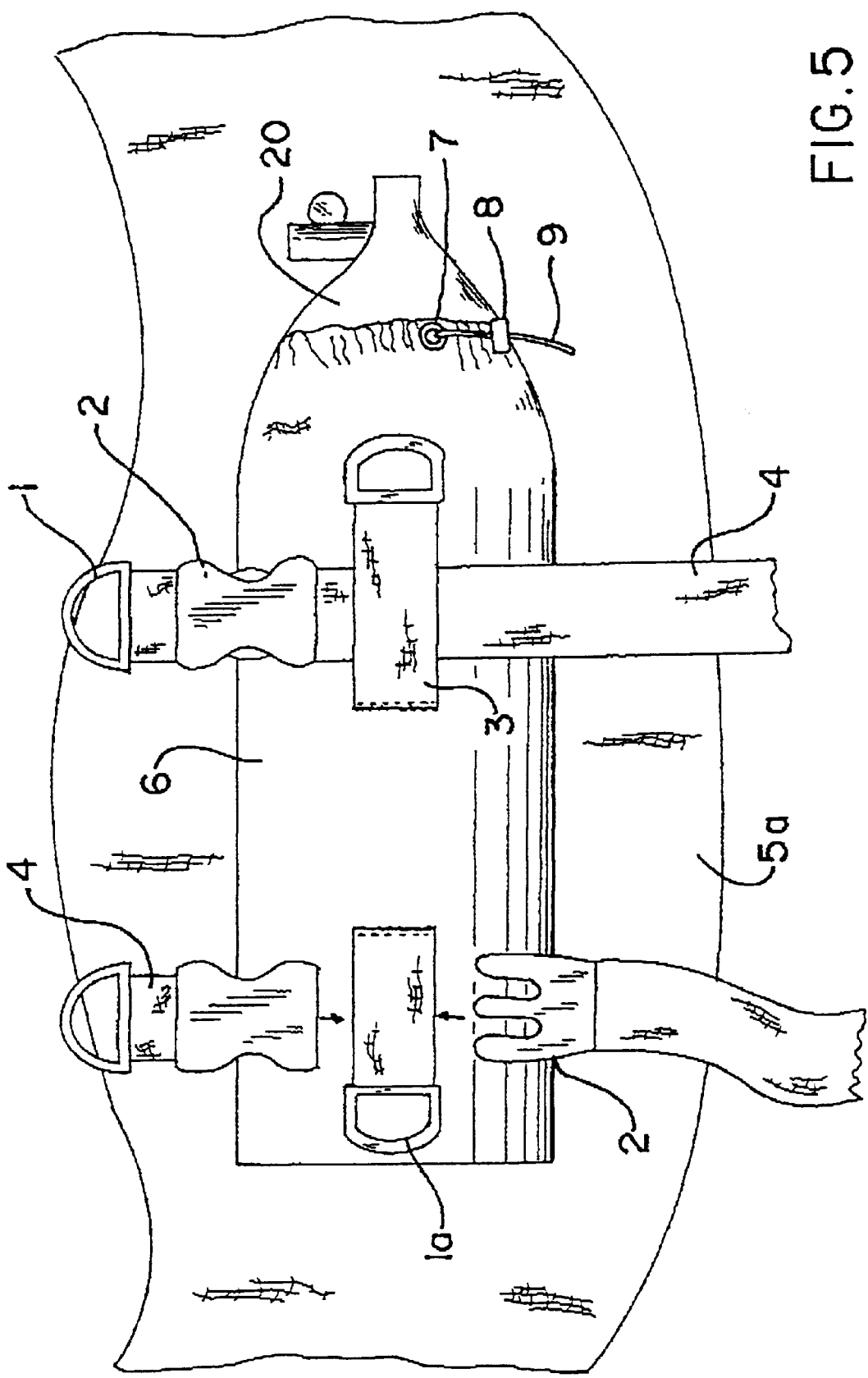
FIG. 5 is a rear view of lumbar oxygen carrier.

At the rear of the belt (see FIG. 5) is a padded portion 5a that is so placed as to be in contact with the lower region of the back known as the lumbar region, generally in the area of the small of the back. This padded portion may be attached to the belt by various means. It is thought that the pad may be separately stitched against the belt or the pad may be constructed as one piece being contiguous with the belt. The pad should be generally sized and shaped to conform to this area of the human back. FIGS. 4 and 5 show the general location of the padded portion 5a while FIGS. 2 and 3 show the padded portion in cross section.

Figure 6:
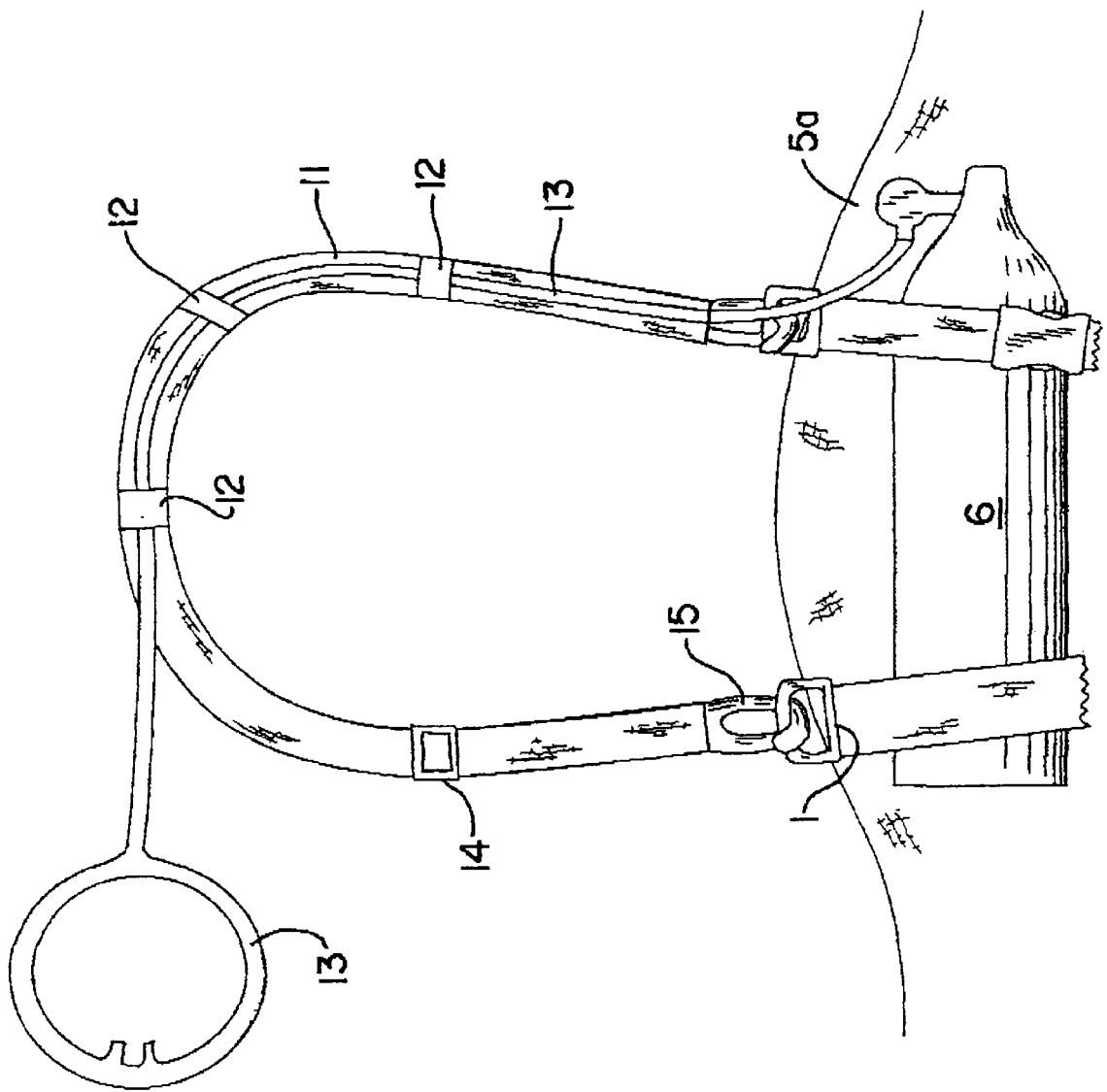
FIG. 6 is a rear view of the strap.
Figure 8:
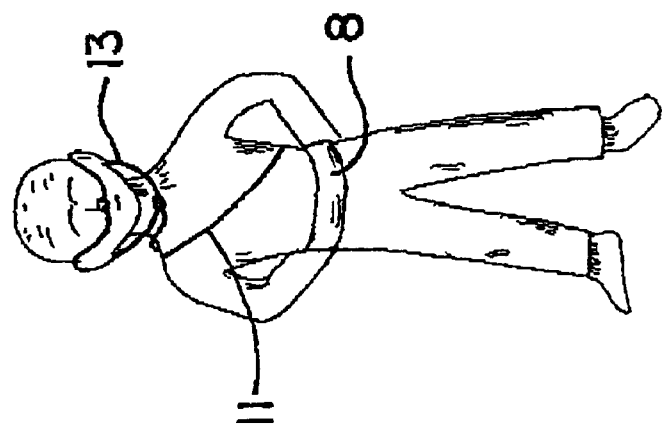
FIG. 8 is a view of apparatus in use on a person.

The pad may have a padded cushion on the inside and be surround by fabric such as leather, burlap, plastic or similar materials on the other sides. Other methods of construction for the pad are possible without varying from the spirit of the invention. There are two D rings 1 at the top of the padded portion 5a (see FIGS. 5 and 6) for attachment of the shoulder strap 11 by means of hooks 15 or similar means.

In connection with the padded portion will be a pouch 6 or similarly shaped portion for holding the oxygen tank 20. The pouch may be described as having the shape of a tube with an opening at one end for the placement of the oxygen tank. The tube may be of the same material as the belt and it is believed that a strong cloth material such as burlap, nylon, etc. would be appropriate for both belt and pouch.

The tubular section of the pouch will have an axis running through the center (when the pouch is expanded) and this axis would be parallel to that direction that the belt runs. In this manner, the pouch will be aligned with the user's belt and thus the oxygen tank placed therein can be secured lengthwise along the user's back.

The pouch is preferably attached to the belt by means of straps 4 having side release buckles 2 or similar means for attaching to one another. It is preferred that two straps be used to attach the pouch, see FIG. 5, however more straps may be used. Each of these straps 4 should be equipped with buckles 2 so that the length of the straps may be varied as they are tightened around the tank and then secured with the buckles. FIG. 5 shows one of straps already connected by the buckles already attached and the other not yet connected. A portion of each of the straps 4 should be in connection with the belt 5 e.g. by stitching or otherwise making the straps an integral portion of the pouch.

The straps can be attached to the pouch portion by loops 3 that are also in the form of straps that are formed into loops. The loops can be sewn or otherwise attached to the pouch 6 so that the pouch and its straps can be detached from the belt for using the tank separately. i.e. one can detach the pouch and tank from the belt by detaching the straps and then use the tank without the belt. Each of these loops may have D rings 1a, at one end, in order to be attached to clips 15 at each end of the shoulder strap, see FIGS. 5 and 6. These d-rings (those in connection with loops 3) are thus directly attached to the pouch so that the pouch and tank can be carried on the shoulder without the use of the belt. The shoulder strap will come with clips 15 at each end and these can be hooked onto the D-rings and thus carry the tank without need of the belt.

In addition to the straps, there should be a drawstring 9 in connection with the pouch and near the open end of the pouch. The drawstring will be formed out of a portion of the pouch e.g. by a grommet 7 in connection with a hem at the entrance to the pouch. The use of the drawstring will enable the user to tighten the drawstring around the neck of the tank that will be at this section of the pouch once the tank is inserted into the pouch. The drawstring will remain secure by use of a cord lock 8 or similar means for maintaining a cord securely around the neck of the pouch.

The tank will thus be aligned horizontally in contrast to its more normal vertical position so that the longer dimension of the tank will be aligned horizontal to the ground. In this manner, the longer sides of the tank will rest upon the small of the user's back. The pull string will be used to further tighten the pouch around the neck of the tank. see FIG. 5. (Note: the neck of the oxygen tank is near numeral 20.)

Figure 7:
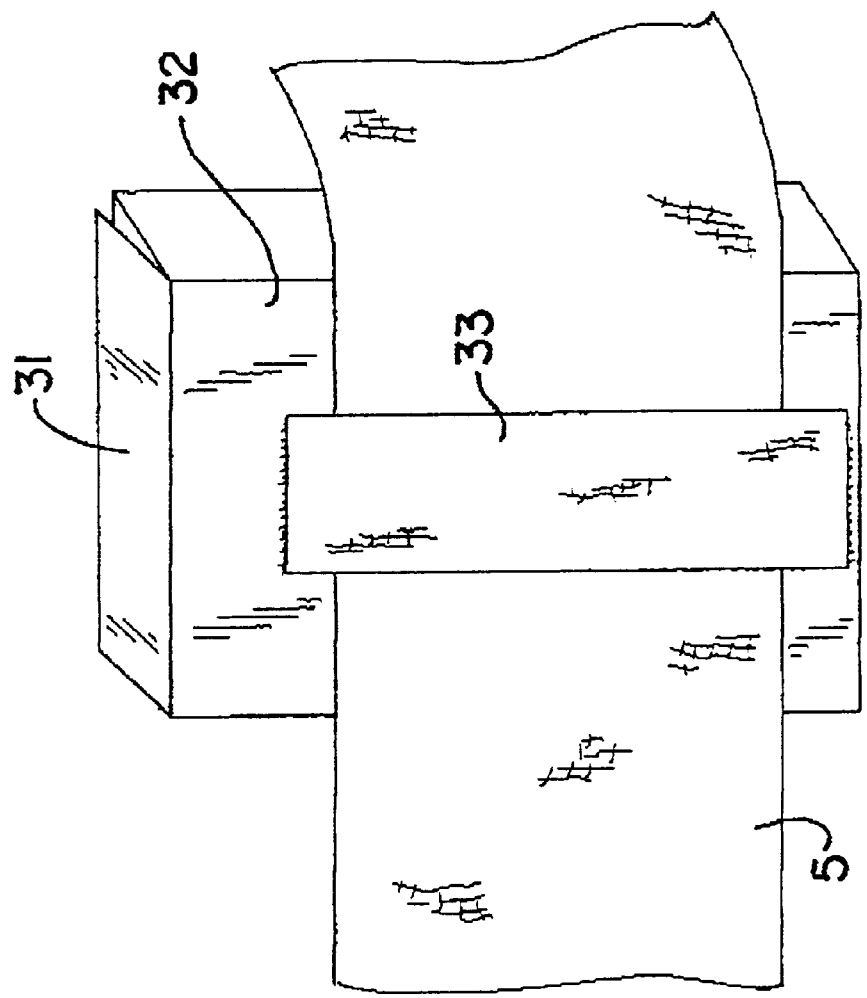
FIG. 7 is a view of the conserver box.

In addition to the pouch there is a smaller pocket for an oxygen conservator box that should be directly attached to the main belt. See FIG. 7. This pocket should be so constructed that it may be detached from the belt when its use would be unnecessary. This includes a pocket 32 for holding the conserver box 31. The pocket should have at least one strap 33 in order to allow the strap to be looped onto the belt 28. The strap would be attached to the pocket by the two ends of the strap.

The support will, preferably, have one shoulder strap in connection with the main belt portion. See FIG. 6. This strap may be worn across the torso of the user by bringing it over one shoulder and head of the client allowing the strap to rest across the opposite shoulder. The strap then goes down and across to that hip that is opposite the shoulder it rests on. Such method is commonly used and is often seen, The strap should be padded at that point where it will cross the user's torso and shoulder for comfort. Other numbers of straps may be used without varying from the spirit of the invention. The strap should be adjustable in nature to account for different sized clients. This may be done through the use of a tribar 14 or similar means for adjusting the length of straps by taking up slack.

The strap would be attached to the belt in two places preferably by means of plastic clips 15 that will allow the strap to be hooked onto a D-ring 1 or similar portion on the belt. Both ends of the strap will be attached to the rear of the belt where the pouch is attached. There should be two D-rings at the top of the rear of the belt in addition to the D rings in connection with the loops.

The oxygen tanks in use typically use a hose and a means for distributing the oxygen to the nostril. This means may be referred to as the cannula 13 in the sense that the cannula brings the oxygen into the patient's nostrils or mouth. Such equipment is well known in the art and need not be described here. The hose may be attached to the shoulder strap by smaller, VELCRO (TM name for hook and loop material mating portions) equipped straps 12 that can be opened and closed to thereby surround the hose 13 and secure the hose to portions of the shoulder strap 11.

It is preferred that at least two such straps 12 be used on the shoulder strap however, this number may be varied without varying from the spirit of the invention. It is preferred that there be one strap at the top of the shoulder strap (near the top of the shoulder) and one strap at a point on the strap where it is connection with the back. In this manner, the straps may be used to support the oxygen hose as it leads from the tank, up the back, and then forward to the user's face.

I claim:

1. A support apparatus for oxygen tanks, the tanks having a hose extending from the tank for supply of oxygen to a user, the apparatus comprising: a belt portion having a front buckle for securing said belt portion to the user's torso and a means for attachment comprising a pair of rear straps at the rear of said belt portion, a pouch being of tubular construction and having at least one open end, said pouch having at least two loop portions for placement of said rear straps to secure said pouch to said belt portion, a shoulder strap in connection with said belt portion and having two ends, each said end having a means for clipping said shoulder strap to said belt portion, said pouch having a drawstring in connection with said pouch for securing said oxygen tank within said pouch.

2. The apparatus of claim 1 wherein said shoulder strap has at least two hose straps for securing the hose of said tank.

3. The apparatus of claim 2 having a padded lumbar portion in connection with said belt portion, said lumbar pad of shape and size to conform to the area of the lower back of the user.

* * * * *